United States Patent
Okandan

(10) Patent No.: US 8,323,955 B1
(45) Date of Patent: Dec. 4, 2012

(54) MICROMACHINED PATCH-CLAMP APPARATUS

(75) Inventor: Murat Okandan, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 2323 days.

(21) Appl. No.: 10/383,163

(22) Filed: Mar. 5, 2003

(51) Int. Cl.
*C12M 1/42* (2006.01)
*C12M 3/00* (2006.01)
*C12N 13/00* (2006.01)

(52) U.S. Cl. .......... 435/285.2; 435/287.1; 435/461; 435/470; 435/173.6; 435/173.1; 435/173.4; 435/173.5; 435/288.3; 435/287.3; 435/305.1

(58) Field of Classification Search .......... 435/287.1, 435/461, 173.6, 173.4, 173.1, 173.5, 285.2, 435/287.3, 288.3, 305.1
See application file for complete search history.

(56) References Cited

U.S. PATENT DOCUMENTS

| | | | | |
|---|---|---|---|---|
| 5,501,893 | A | | 3/1996 | Laermer .................... 428/161 |
| 6,063,260 | A | | 5/2000 | Olesen .................... 205/793 |
| 6,133,670 | A | | 10/2000 | Rodgers .................... 310/309 |
| 6,175,170 | B1 | | 1/2001 | Kota .................... 310/40 MM |
| 6,368,851 | B1 | | 4/2002 | Baumann .................... 435/285.2 |
| 6,379,916 | B1 | | 4/2002 | Meyer .................... 435/29 |
| 6,482,619 | B1 | * | 11/2002 | Rubinsky et al. .......... 435/173.7 |
| 6,507,138 | B1 | | 1/2003 | Rodgers .................... 310/309 |
| 6,645,757 | B1 | * | 11/2003 | Okandan et al. .......... 435/285.1 |
| 6,653,124 | B1 | * | 11/2003 | Freeman .................... 435/297.1 |
| 6,692,456 | B1 | * | 2/2004 | Eppstein et al. .......... 604/22 |
| 6,699,697 | B2 | * | 3/2004 | Klemic et al. .......... 435/173.4 |
| 6,942,169 | B2 | * | 9/2005 | Sparks .................... 241/1 |
| 2002/0064841 | A1 | | 5/2002 | Klemic .................... 435/164 |
| 2002/0108869 | A1 | | 8/2002 | Savtchenko .......... 205/777.5 |
| 2002/0164777 | A1 | | 11/2002 | Kelly .................... 435/287.1 |
| 2002/0182627 | A1 | * | 12/2002 | Wang et al. .......... 435/6 |
| 2003/0032946 | A1 | * | 2/2003 | Fishman et al. .......... 604/890.1 |
| 2003/0098248 | A1 | * | 5/2003 | Vogel et al. .......... 205/777.5 |
| 2003/0107386 | A1 | * | 6/2003 | Dodgson et al. .......... 324/699 |
| 2005/0158845 | A1 | * | 7/2005 | Wikswo et al. .......... 435/287.1 |
| 2006/0003310 | A1 | * | 1/2006 | Klauke et al. .......... 435/4 |

OTHER PUBLICATIONS

C. Schmidt, M. Mayer and H. Vogal, "*A Chip-Based Biosensor for the Functional Analysis of Single Ion Channels*," Angew.Chem.Int.Ed. 2000, 39, No. 17 pp. 3137-3140.
Y. Huang and B. Rubinsky, "*Microfabricated electroporation chip for single cell membrane permeabilization,*" Sensor and Actuators A 89 (2001) 242-249.
K.G. Klemic, J.F. Klemic, M.A. Reed, F.J. Sigworth, "*Micromolded PDMS planar electrode allows patch clamp electrical recordings from cells,*" Biosensors and Bioelectronics 17 (2002) pp. 597-604.
M. Okandan, D. Salas, P. Galambos, S. S. Mani, K. Zavadil, "*Micromachined Patch Clamp Array,*" SAND Report SAND2002-0925, Jun. 2002.
D.L. Ypey and L.J. DeFelice, "*The Patch-Clamp Technique: A Theoretical and Practical Introduction Using Simple Electrical Equivalent Circuits,*" Dec. 11, 1999 http://www.biophysics.org/btol/img/ypey-Parts_123.pdf.

* cited by examiner

*Primary Examiner* — Nathan Bowers
(74) *Attorney, Agent, or Firm* — Olivia J. Tsai

(57) ABSTRACT

A micromachined patch-clamp apparatus is disclosed for holding one or more cells and providing electrical, chemical, or mechanical stimulation to the cells during analysis with the patch-clamp technique for studying ion channels in cell membranes. The apparatus formed on a silicon substrate utilizes a lower chamber formed from silicon nitride using surface micromachining and an upper chamber formed from a molded polymer material. An opening in a common wall between the chambers is used to trap and hold a cell for analysis using the patch-clamp technique with sensing electrodes on each side of the cell. Some embodiments of the present invention utilize one or more electrostatic actuators formed on the substrate to provide mechanical stimulation to the cell being analyzed, or to provide information about mechanical movement of the cell in response to electrical or chemical stimulation.

1 Claim, 10 Drawing Sheets

Section 3 - 3

Section 1 - 1

Section 2 - 2

Section 3 - 3

MICROMACHINED PATCH-CLAMP APPARATUS

GOVERNMENT RIGHTS

This invention was made with Government support under Contract No. DE-AC04-94AL85000 awarded by the U.S. Department of Energy. The Government has certain rights in the invention.

CROSS REFERENCE TO RELATED INVENTIONS

This patent application is related to co-pending patent application Ser. No. 09/779,164 which is incorporated herein by reference.

FIELD OF THE INVENTION

The present invention relates generally to devices for studying or analyzing biological cells, and in particular to a micromachined apparatus for holding one or more biological cells to allow electrophysiological evaluations thereof based on the patch-clamp technique.

BACKGROUND OF THE INVENTION

The patch-clamp technique was originally developed to study cell membrane electrophysiology by measuring very small ($10^{-9}$-$10^{-12}$ A) electrical currents that can flow through ion channels embedded in the lipid bilayers that form cell membranes. Such ion channels, which are typically made of proteins or assemblies of proteins, control the flow of ions (e.g. $Na^+$, $K^+$, $Ca^{2+}$) in and out of biological cells, with the flow of ions producing weak, but measurable, electrical currents that can be sensed and recorded using the patch-clamp technique. The ion channels communicate electrical, mechanical (i.e. tactile) and chemical information into and out from biological cells and thereby participate in many different cellular processes which include the generating and timing of action potentials, the secretion of hormones, synaptic transmission, and the triggering of muscular contractions. Thus, the patch-clamp technique provides a way of determining or analyzing the effect of external electrical, mechanical or chemical stimuli on cells, and the response of the cells to such external stimuli. The patch-clamp technique, for which Neher and Sakmann were awarded the 1991 Nobel Prize in Physiology and Medicine, is useful for performing electrophysiological studies of cells to better understand cell behavior in response to external or internal stimuli, to understand exactly how the cell membrane functions, to understand certain ion-channel-related diseases and disorders, and to screen potential drug candidates for the treatment of ion-channel-related diseases and disorders or their effect on biological cells.

The patch-clamp technique is conventionally performed using a glass micropipette which must be mechanically manipulated to contact a single biological cell and to establish a "Giga-Ohm" seal with a membrane of the cell, generally by a specially-trained operator gently sucking onto the other end of the micropipette. This conventional use of the patch-clamp technique is tedious and allows the analysis of only a few cells per day.

What is needed is an apparatus that can be used to perform the patch-clamp technique under better-controlled conditions and with higher speed and precision. Additionally, it would be advantageous to have a patch-clamp apparatus that would use of smaller amounts of fluids that surround the cell and interact with it, including particular chemical species provided to stimulate the cell. Finally, what is needed is a patch-clamp apparatus that can be readily adapted to provide various types of external stimulation, including mechanical stimulation.

The present invention provides a micromachined patch-clamp apparatus that can be used for the electrophysiological study of one or more cells in a closed environment with a minimal volume (as small as a few nanoliters) of fluids surrounding and contacting the cell. The present invention is also adaptable for use with microelectromechanical actuators to provide, in certain embodiments, an instrument capable of subjecting a cell to mechanical stimulation in addition to electrical and chemical stimulation.

These and other advantages of the present invention will become evident to those skilled in the art.

SUMMARY OF THE INVENTION

The present invention relates to a micromachined patch-clamp apparatus for analyzing one or more biological cells. The apparatus comprises a silicon substrate and a pair of fluid chambers formed above the silicon substrate, with a common wall formed of silicon nitride being located between the pair of fluid chambers and having an opening (e.g. 1-10 μm in size) therethrough. A lower chamber of the pair of fluid chambers has one or more electrodes therein comprising polycrystalline silicon. An upper chamber of the pair of fluid chambers comprises a molded polymer material that forms a top and a sidewall of the upper chamber for receiving the biological cells. The apparatus preferably includes means for urging the biological cell being analyzed into contact with the common wall and the opening therethrough which can comprise either a fluid evacuation port connected to the lower chamber, or a fluid entry/exit port connected to the upper chamber. The upper chamber can further include a sample entry/exit port for introducing the biological cells into the upper chamber and for removing the biological cells after analysis.

The molded polymer material used to form the top and sidewall(s) of the upper chamber can comprise a silicon elastomer (e.g. poly-dimethylsiloxane also termed herein PDMS) and can include a reference electrode for providing an electrical connection to any biological cell located therein. In operation of the apparatus, the common wall forms a high-resistance seal for a cell membrane covering the opening in the common wall to allow electrical current measurements to be made using the electrodes which in electrical connection with the biological cell through a fluid surrounding the cell in the upper and lower chambers. An optical access port can be formed through the silicon substrate below the opening for viewing the biological cell. Certain embodiments of the present invention can further include an electrostatic actuator (e.g. an electrostatic comb actuator or a capacitive-plate electrostatic actuator) that is operatively connected to provide mechanical stimulation to one or more biological cells being analyzed.

The present invention further relates to a micromachined patch-clamp apparatus that comprises a silicon substrate; a first fluid chamber formed above the substrate from a plurality of deposited and patterned layers of silicon nitride; a second fluid chamber formed above the first fluid chamber, with the second fluid chamber comprising a molded polymer material (e.g. a silicone elastomer such as PDMS) wherein the biological cell is located for analysis thereof; an opening formed between the first and second fluid chambers for capturing the biological cell being analyzed; and electrical connections (e.g. comprising one or more deposited and patterned layers of polycrystalline silicon) to the first and second fluid chambers for determining an electrical characteristic of the cell being analyzed. The apparatus can further include an optical access port formed through the silicon substrate below the opening for viewing a biological cell located within the second fluid chamber.

A fluid evacuation port can be provided to the first fluid chamber; and a fluid entry/exit port can be provided to the second fluid chamber which also can include a sample entry/exit port for introducing one or more biological cells into the apparatus and for removing the cells from the apparatus (e.g. by reversing the flow of a fluid in the apparatus). The opening between the first and second chambers is sized to be smaller than the size of the biological cells being analyzed so that the cells can be held in place about the opening by a pressure differential in the fluid in the two chambers. As an example, the size of the opening between the first and second chambers can have lateral dimensions of 1-10 μm.

The present invention also relates to a micromachined patch-clamp apparatus that comprises a silicon substrate; a pair of fluid chambers formed above the silicon substrate, with the pair of fluid chambers having a common wall oriented parallel to the plane of the substrate, with the common wall comprising silicon nitride and having an opening therethrough between the pair of fluid chambers, and with a lower chamber of the pair of fluid chambers having at least one electrode therein, and with an upper chamber of the pair of fluid chambers comprising a molded polymer material and being adapted to receive one or more biological cells for analysis thereof; and an electrostatic actuator operatively connected to provide mechanical stimulation to the biological cells located in the upper chamber.

Additional advantages and novel features of the invention will become apparent to those skilled in the art upon examination of the following detailed description thereof when considered in conjunction with the accompanying drawings. The advantages of the invention can be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several aspects of the present invention and, together with the description, serve to explain the principles of the invention. The drawings are only for the purpose of illustrating preferred embodiments of the invention and are not to be construed as limiting the invention. In the drawings.

DETAILED DESCRIPTION OF THE INVENTION

The present invention provides an apparatus 10 for carrying out the well-known patch-clamp technique for studying one or more cells 100, and is referred to hereinafter as a patch-clamp apparatus 10. Further details of the patch-clamp technique can be found in an article by D. L. Ypey and L. J. DeFelice entitled "The Patch-Clamp Technique: A Theoretical and Practical Introduction Using Simple Electrical Equivalent Circuits" available on the world-wide web at the following address: http://www.biophysics.org/btol/img/Ypey-Parts123.pdf. The patch-clamp technique is also disclosed in U.S. Pat. Nos. 6,063,260 and 6,379,916 which are incorporated herein by reference.

Figure 1:
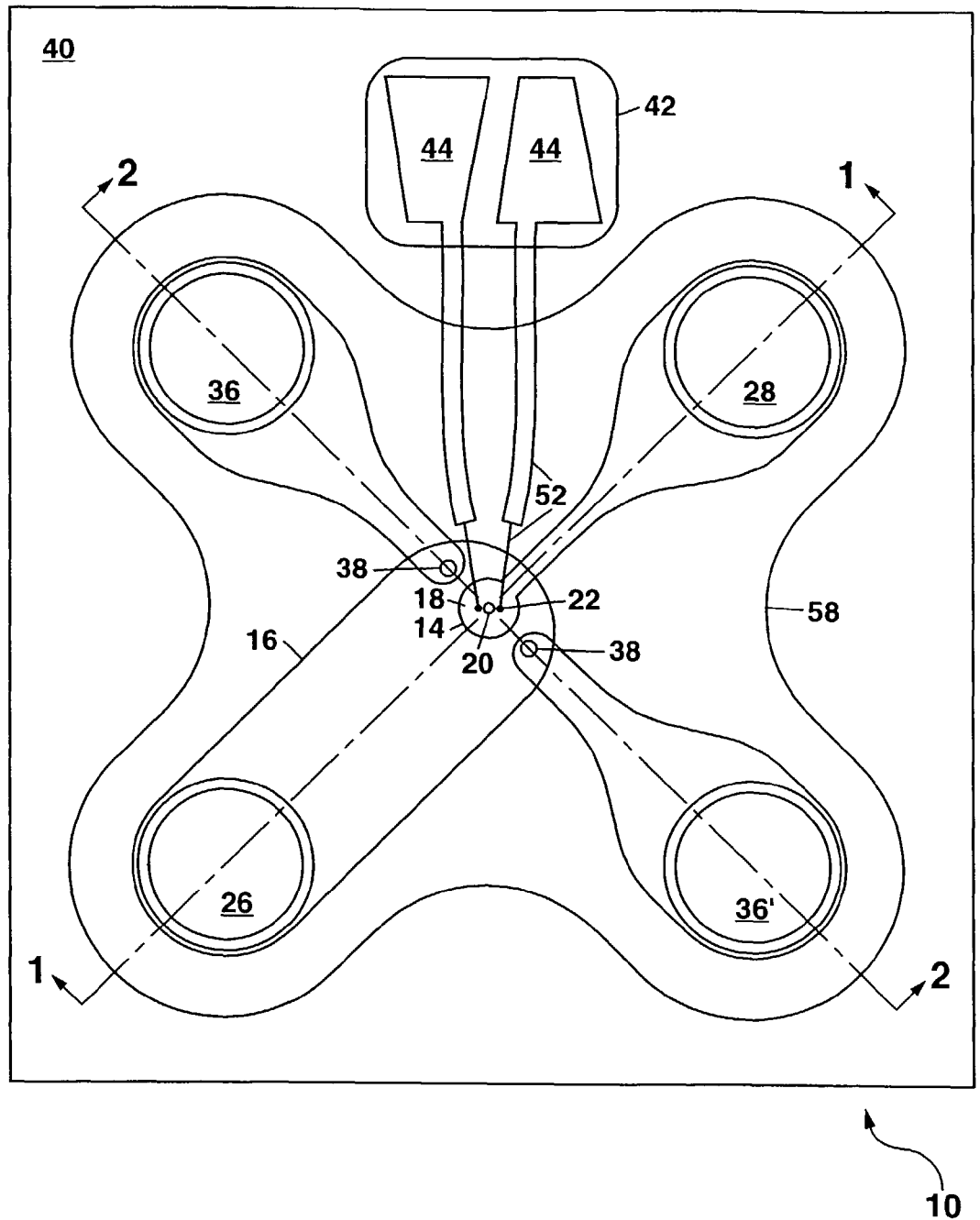
FIG. 1 shows a schematic plan view of a first embodiment of the micromachined patch-clamp apparatus of the present invention.
Figure 2A:
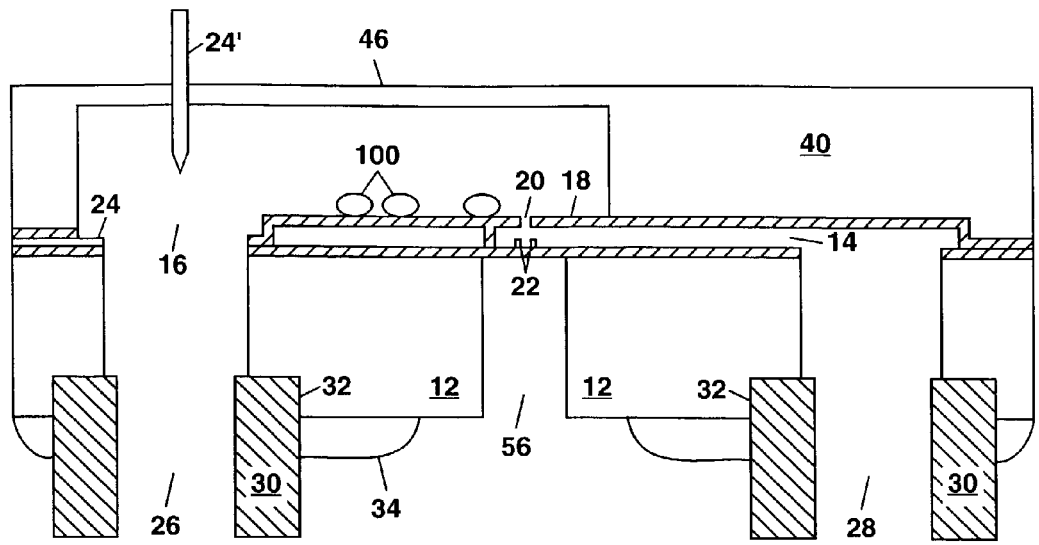
FIGS. 2A and 2B show schematic cross-section views of the device of FIG. 1 along the section lines 1-1 and 2-2, respectively.
Figure 2B:
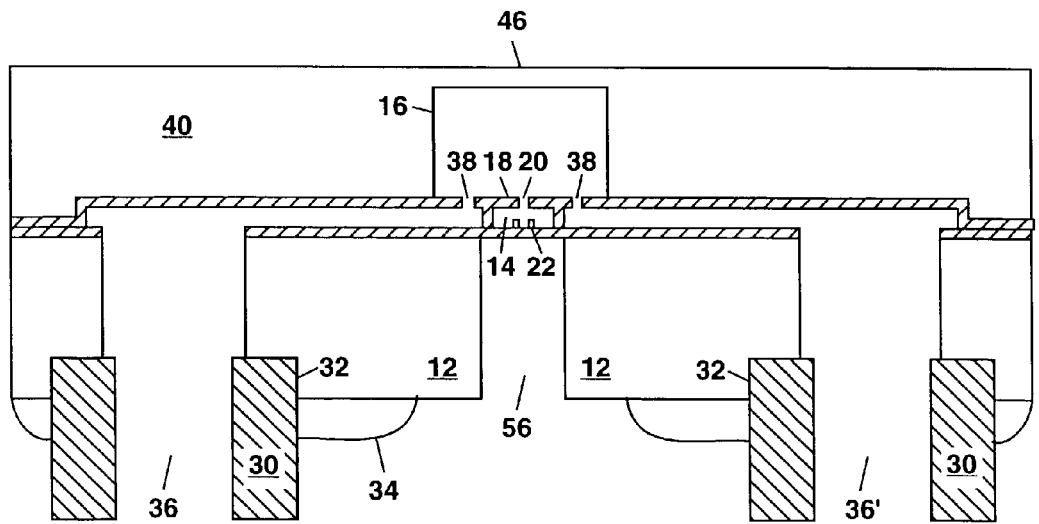

FIGS. 1 and 2A, 2B schematically illustrate in plan view and cross-section views, respectively, a first embodiment of the patch-clamp apparatus 10 of the present invention. The apparatus 10 in FIGS. 1 and 2A, 2*b* comprises a silicon substrate 12, with a pair of fluid chambers being formed above the substrate 12, including a lower chamber 14 and an upper chamber 16 separated by a common wall 18 which preferably comprises silicon nitride and which is oriented parallel to the plane of the substrate 12. The common wall 18 includes an opening 20 between the lower and upper chambers, 14 and 16, with the opening 20 being smaller than the cells 100 being analyzed. Generally, the opening 20 is micron-sized (e.g. 1-10 μm across).

The opening 20 is used to localize the cell membrane and to provide a high-resistance seal to the cell 100 so that electrical connections can be made to measure minute (nanoampere to picoampere) electrical currents that flow through the cell membrane (i.e. through ion channels therein) in response to internal processes or external electrical, mechanical or chemical stimuli, or a combination thereof. These electrical connections can be made through one or more electrodes 22 that are located within the lower chamber 14 and through a reference electrode 24 which can be located within the upper chamber 16, or alternately outside the upper chamber 16 but in electrical contact with the upper chamber 16 and the cell 100 through an electrically-conducting fluid disposed within the upper chamber 16. The term "membrane" is used herein to designate whole cells or partial cell membranes.

The reference electrode 24 can be formed from the substrate 12, or from a layer of polycrystalline silicon (also termed polysilicon) deposited on the substrate 12 (e.g. on a silicon nitride layer that acts to provide electrical insulation from the substrate 12). An electrical connection to the reference electrode 24 can be made to the substrate 12 or to a contact pad 44 (not shown) depending on whether the reference electrode 24 is formed from the substrate 12 or from a polysilicon layer electrically insulated from the substrate 12. In some embodiments of the present invention, the reference electrode 24 can be located within a port providing a fluid connection to the upper chamber 16. In other embodiments of the present invention, the reference electrode can comprise a metal electrode 24' (e.g. comprising platinum or silver/silver chloride) which can be embedded in or inserted through the molded polymer material 40 to contact the fluid disposed therein. The use of an optional metal reference electrode 24' is indicated in FIG. 2A. The metal reference electrode 24' can be pointed as shown in FIG. 2A so that it can be inserted through the molded polymer material 40 and later removed, if needed.

In the first embodiment of the present invention in FIG. 1 and FIGS. 2A, 2B, fluid connections to the patch-clamp apparatus 10 can be made through the silicon substrate 12. These fluid connections include a sample entry/exit port 26 and a fluid evacuation port 28. The sample entry/exit port 26 can be used to introduce one or more biological cells 100 and a surrounding fluid into the upper chamber 16 of the apparatus 10. The surrounding fluid can comprise an electrically conductive buffer solution provided from a fluid reservoir connected to the port 26. A vacuum source (not shown) can be connected to the evacuation port 28 using microcapillary tubing 30 to provide a difference in pressure in the fluid in the two chambers 14 and 16. This pressure differential produces a flow of the fluid between the two chambers 14 and 16 and urges the cells 100 towards the opening 20 where one of the cells 100 will be captured by blocking the opening 20. This will produce an increase in the pressure differential which will urge the captured cell 100 into a more intimate contact with the common wall 18 thereby forming a high-resistance seal (generally termed a gigaohm seal or a giga-seal) which is needed to prevent the flow of an electrical current around the cell 100 and to limit any flow of the current to the ion channels within the cell membrane which are the object of study using the patch-clamp technique. The pressure differential used for positioning and capturing the cell 100 to be analyzed can also be generated or augmented by providing a positive pressure of the fluid to the sample entry/exit port 26 (e.g. with a pump).

In FIG. 2A, the microcapillary tubing 30 can be inserted into a counterbored portion 32 of the substrate 12 which, together with openings completely through the substrate 12 at the locations of the various ports, can be formed by a deep anisotropic plasma etching process as is disclosed, for example, in U.S. Pat. No. 5,501,893 to Laermer which is incorporated herein by reference. The microcapillary tubing 30 can be fastened to the substrate 12 with a manually-applied coating 34 of a curable polymer material such as PDMS, or alternately with an adhesive (e.g. epoxy).

In FIGS. 1 and 2B, one or more additional fluid entry/exit ports 36 can be provided to introduce particular chemical species (e.g. chemical substances or compounds such as drugs or test chemicals) from liquid dispensers (not shown) into the presence of a cell 100 being examined for measuring an electrical characteristic of the cell 100 to the presence of the chemical species using the patch-clamp technique. The chemical species, which can be provided to the entry/exit ports 36 under positive pressure, can flow into the upper chamber 16 through orifices 38 which are preferably smaller than the cells 10 being analyzed, and which can be the same size or larger than the opening 20 through the common wall 18 (e.g. when the opening 20 is 2-3 µm wide, the orifices 38 can be 5 µm wide). In some embodiments of the present invention, the orifices 38 can be slotted (see FIG. 6). The provision of a pair of entry/exit ports 36 and 36' as shown in FIGS. 1 and 2B also allows the chemical species to be introduced through one port 36 and then evacuated through the other port 36' thereby providing a continuous flow of the chemical species across the cell 100. This arrangement can allow the cell 10 being studied to be exposed a sequence of different chemical species, or to different concentrations of a given chemical species over time.

The upper chamber 16 in FIGS. 1 and 2A, 2B can be formed from a molded polymer material 40 which preferably comprises a silicone elastomer such as poly-dimethylsiloxane (PDMS) which is also termed poly(dimethylsiloxane). The PDMS is optically transparent and can be spun onto a mold 200 to form the polymer material 40 with a shape shown in FIGS. 1 and 2A, 2B.

Figure 3A:
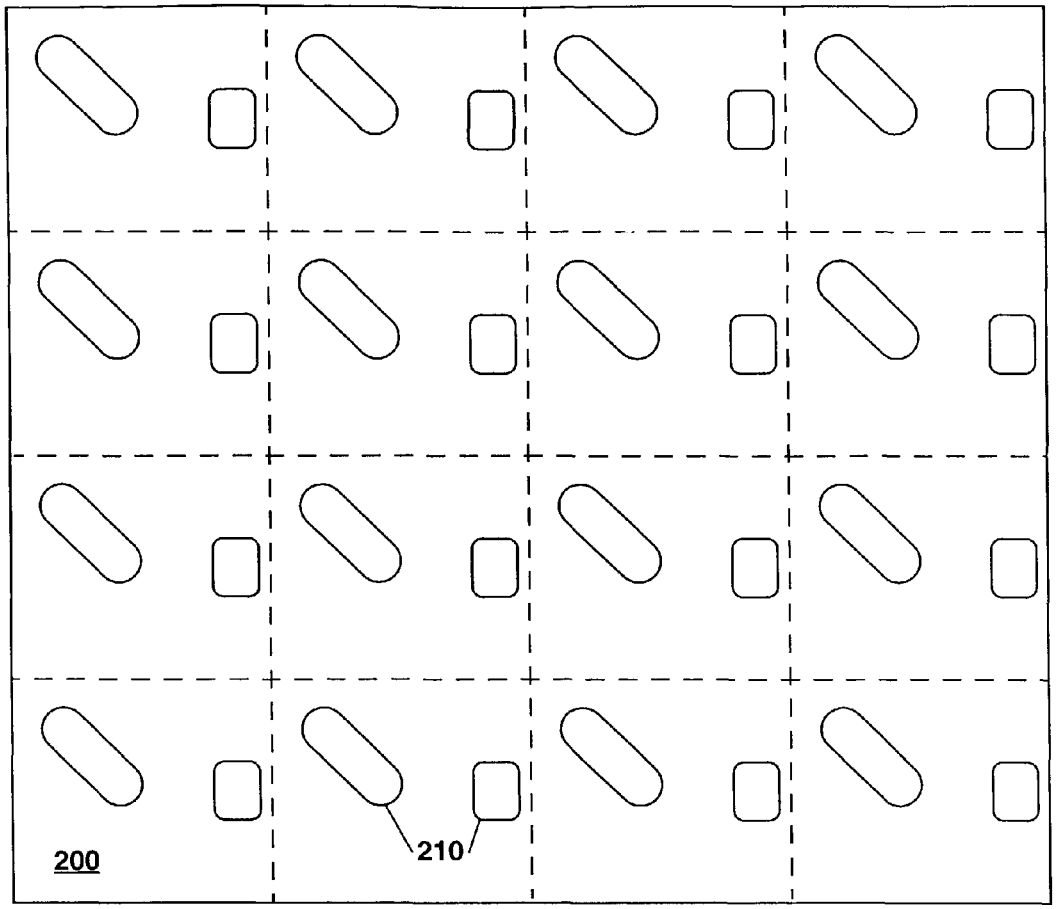
FIGS. 3A and 3B show a plan view and a side view, respectively, of a mold that can be used to form the molded polymer material that is provided over the substrate to complete the device of FIG. 1.
Figure 3B:
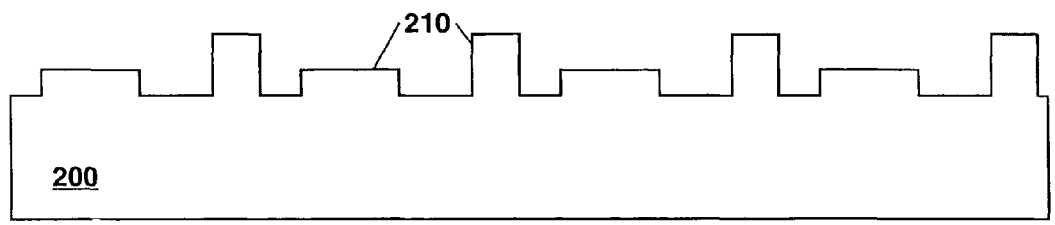

To form the molded polymer material 40 into the shape of the upper chamber 16 and to provide one or more openings 42 to contact pads 44 (i.e. probe or bond pads) on the substrate 12, the mold 200 can be formed, for example, by photolithographic masking and anisotropic etching a silicon wafer (see FIGS. 3A and 3B) to form topographical features 210 in the surface of the silicon wafer corresponding to the shapes of the upper chamber 16 and the openings 42 to be formed in the molded polymer material 40. The anisotropic etching can be performed by reactive ion etching or by a Bosch process as will be described hereinafter. The mold 200 can be used to form a plurality of pieces of the molded polymer material 40 in a batch process with the individual pieces of the molded polymer material 40 being cut apart along the dashed lines in FIG. 3A after curing of the material 40.

Different etch depth variations in the silicon wafer mold 200 can be used to create a larger or smaller fluid cavity in the spun-on polymer material 40 for forming the upper chamber 16. As an example, the upper chamber 16 in FIGS. 1 and 2A, 2B can have inside lateral dimensions of 200 µm×700 µm and can be 50-100 µm high. The thickness of a top 46 of the upper chamber 16 can be, for example, 10-1000 µm, with the top 46 forming an optical window for microscopically viewing the position of the cells 100 when they are introduced into the apparatus 10.

Once the mold 200 has been prepared, the polymer material in an uncured state can be spun onto the mold 200 using a conventional spin coating machine as known to the semiconductor processing art. As an example, PDMS can be spin coated onto the mold 200 with the mold 200 being rotated at 2000 revolutions per minute (rpm). The spun-on polymer material 40 can then be cured at an elevated temperature for a predetermined time (e.g. 80° C. for one hour for PDMS), and then peeled from the mold, cut apart along the dashed lines in FIG. 3A and positioned over the substrate 12 to form the completed apparatus 10 of FIGS. 1 and 2A, 2B. Once aligned over the patterned silicon nitride layers forming the lower chamber 14 and channels to the fluid entry/exit ports 36 and 36', the molded polymer material 40 can then be pressed into place on the substrate 12. Surface tension holds the molded polymer material 40 in place on the substrate 12 and allows the material 40 to be removed and reattached up to several times, if needed.

FIGS. 4A-4I illustrate fabrication of the patch-clamp apparatus 10 in FIGS. 1 and 2A, 2B except for the molded polymer material 40 using conventional surface micromachining processes. Surface micromachining, which is based on a series of process steps used to fabricate integrated circuits (ICs), comprises depositing and patterning a plurality of material layers one after another to build up the structure of a particular micromachined device layer by layer. For the present invention, the deposited and patterned material layers comprise silicon nitride, polysilicon (i.e. polycrystalline silicon), and a sacrificial material such as silicon dioxide ($SiO_2$) or a silicate glass (e.g. TEOS which is deposited from the decomposition of tetraethylortho silicate by low-pressure chemical vapor deposition at about 750° C. followed by densification at a higher temperature). The term "patterning" as used herein refers to a sequence of well-known IC processing steps including applying a photoresist to the substrate 12, prebaking the photoresist, aligning the substrate 12 with a photomask, exposing the photoresist through the photomask, developing the photoresist to form an etch mask, baking the substrate 12, partially or completely etching away the surfaces of material layers not protected by the etch mask, and stripping the etch mask so that further processing or deposition can take place. In some cases, a hard etch mask formed from silicon nitride, silicon dioxide or TEOS can be substituted for the photoresist etch mask (e.g. when etching deeper than a few microns).

Figure 4A:
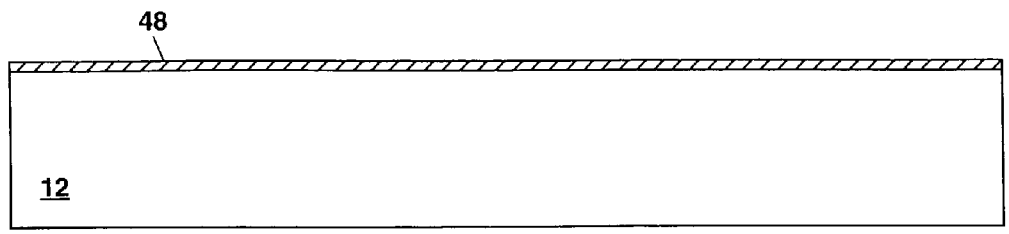
FIGS. 4A-4I show schematic cross-section views of the device of FIG. 1 along the section line 1-1 to illustrate fabrication of the apparatus except for the molded polymer material using conventional surface micromachining processes.

In FIG. 4A, in preparation for forming a micromachined portion of the device 10 of FIGS. 1 and 2A, 2B, the silicon substrate 12 can be initially prepared by coating the substrate 12 with a thermal oxide film (not shown) which can be, for example, 0.6 μm thick. A first silicon nitride layer 48, which can be 0.8 μm thick, can then be blanket deposited over the substrate 12 by low-pressure chemical vapor deposition (LPCVD). The first silicon nitride layer 48 is used in building the structure of the lower chamber 14 and for insulating the electrodes 22 and 24 from the substrate 12.

Figure 4B:
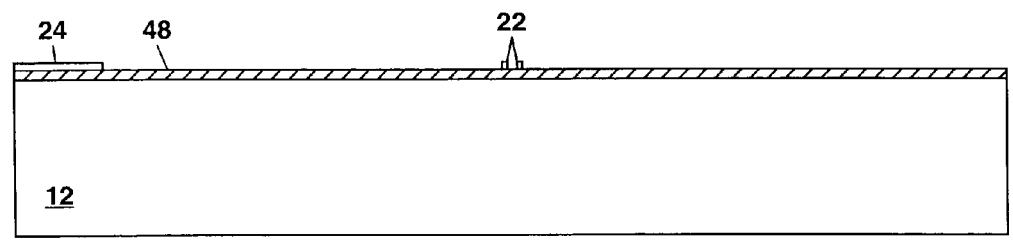

In FIG. 4B, a layer of phosphorous-doped polysilicon can be blanket deposited over the substrate 12 by LPCVD at 580° C. and then patterned using reactive ion etching to form the electrodes 22 and 24. This polysilicon layer can be, for example, 0.3 μm thick. Patterning of the polysilicon layer is also used to form electrical wiring 52 between the electrodes 22 and 24 and the contact pads 44 on the substrate 12. For embodiments of the present invention including additional polysilicon layers (see FIGS. 6 and 7), each additional polysilicon layer can be deposited over the substrate 12 by LPCVD at 580° C. with a layer thickness up to about 2 μm.

The electrical impedance of the wiring 52 for each pair of electrodes 22 is preferably matched. This can be done, for example, by making the wiring 52 to each electrode 22 with the same dimensions and shape, or with mirror-image shapes. As shown in FIG. 1, the wiring 52 to the electrodes 22 can be necked down to about a small feature size (e.g. 1 μm in width) to facilitate connecting the wiring 52 to the electrodes 22 which can be, for example, circular with a diameter of 2-3 μm. The electrodes 22 are preferably centered about the opening 20 through the common wall 18 to facilitate accurate and reproducible measurements, using the patch-clamp technique.

Figure 4C:
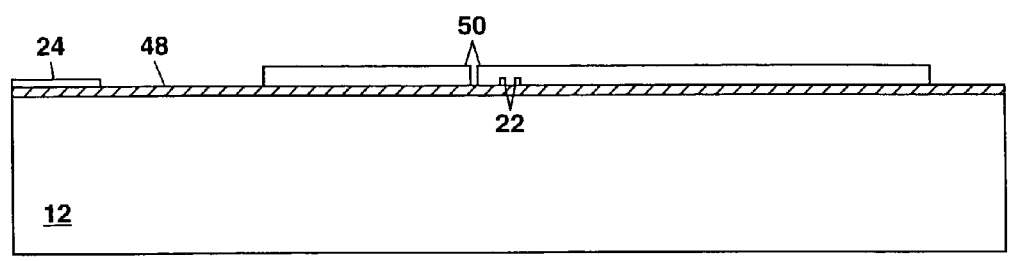

In FIG. 4C, a layer of a sacrificial material 50 (e.g. $SiO_2$ or TEOS) can be blanket deposited over the substrate 12 by chemical vapor deposition (CVD) and patterned by reactive ion etching to define the shape of the lower chamber 14 which extends outward from the opening 20 to the evacuation port 28, the shape of passages between the inlet/outlet ports 36 and 36' and the orifices 38, and any other areas of the device 10 wherein a subsequently-deposited second silicon nitride layer 54 is to be spaced apart from the first silicon nitride layer 48. The layer of the sacrificial material 50, which is used to define the height of the lower chamber 14, can be, for example, 2 μm thick.

The thickness and planarity of the layer of the sacrificial material 50 in FIG. 4C can be precisely controlled by using a chemical-mechanical polishing (CMP) step after blanket deposition of the sacrificial material 50 and prior to patterning thereof. The use of chemical-mechanical polishing for planarizing deposited layers in surface micromachining is well known in the art and has been disclosed, for example, in U.S. Pat. No. 5,804,084 to Nasby, which is incorporated herein by reference.

Figure 4D:
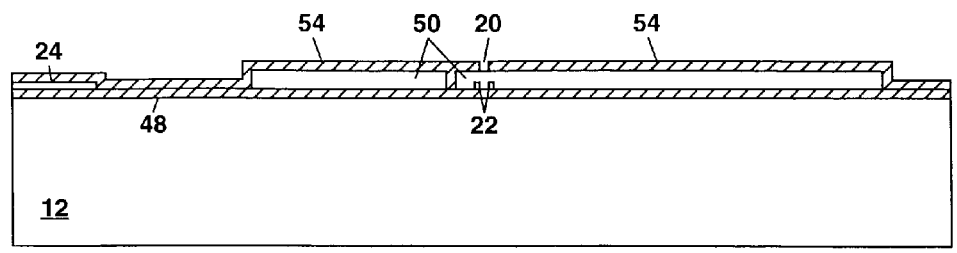

In FIG. 4D, a second silicon nitride layer 54 can be blanket deposited over the substrate 12 by LPCVD and then patterned to form the openings 20 and orifices 38 (see FIG. 2B). The second silicon nitride layer can be, for example, 0.8 μm thick. In some embodiments of the present invention, an additional silicon nitride layer can be deposited and laminated over the second silicon nitride layer 54 to increase the thickness of the common wall 18 to, for example, 1.6 μm to provide added strength.

Figure 4E:
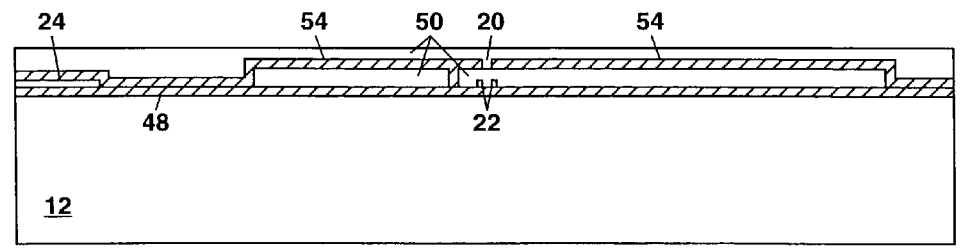

In FIG. 4E, another layer of the sacrificial material 50 can be blanket deposited over the substrate 12 by CVD and planarized by CMP to protect a topside of the substrate 12 during formation of the various ports 26, 28, 36 and 36' through the substrate 12 from a backside thereof. This layer of the sacrificial material 50 can be, for example, 2 μm thick. With the various layers of the device 10 encapsulated within the sacrificial material 50, an annealing step can be performed for reducing stress within the polysilicon and silicon nitride layers. This annealing step can be performed at an elevated temperature of about 1100° C. for several hours. Additional annealing steps can be performed as needed for any subsequently deposited and patterned polysilicon layers (see FIGS. 6 and 7), with each annealing step preferably being performed after the polysilicon layers are encapsulated by an overlying blanket-deposited layer of the sacrificial material 50.

Figure 4F:
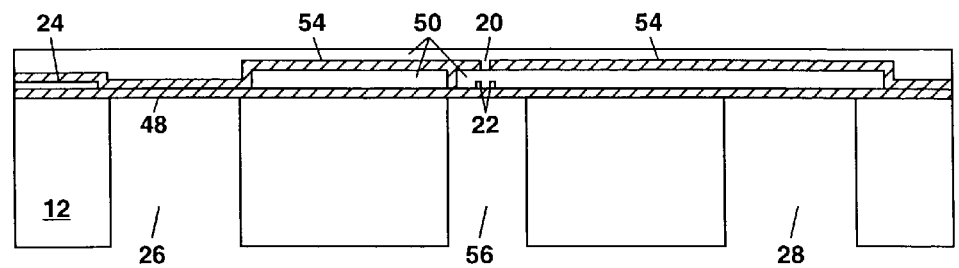

In FIG. 4F, the various ports 26, 28, 36 and 36' and an optical access port 56 can be etched through the substrate 12 using an etch mask which can be formed on the backside of the substrate 12. The optical access port 56 is centered below the opening 20 and is useful for viewing the biological cell 100 during capture and analysis with the apparatus 10. The optical access port 56, which can be up to a few hundred microns in diameter, can also be used for backside illumination when the cell 100 is viewed through the top 46 of the upper chamber 16, or for laser or lamp excitation of the cell 100 or portions therein when fluorescent tagging is used. Additionally, the optical access port 56 allows optical transmission measurements to be made for the cell 100 and surrounding fluid through the lower and upper chambers, 14 and 16. Although the polysilicon electrodes 22 and vertical portions of the second silicon nitride layer 54 are generally not transparent, this is not detrimental to use of the optical access port 56 since these elements account for only a small portion of the overall viewable region provided by the optical access port 56.

Although not shown in FIGS. 2A, 2B and 4A-4F, when LPCVD and CVD are used to deposit silicon nitride, polysilicon and the sacrificial material on the topside of the substrate 12, these deposition processes also blanket deposit the same thickness of these materials on the backside of the substrate 12. Therefore, a hard etch mask can be formed on the backside of the substrate 12 by patterning the silicon nitride, polysilicon and sacrificial material layers that are already present on the backside of the substrate 12 at this stage in the fabrication process. This hard etch mask can then be used for a deep anisotropic plasma etch step (also termed a Bosch etch) through the substrate 12 to form the various ports 26, 28, 36 and 36' and the optical access port 56. Each of these ports can be, for example, 100 μm in diameter. The Bosch etch process is disclosed in U.S. Pat. No. 5,501,893 to Laermer which is incorporated herein by reference. This Bosch etch process combines multiple anisotropic etching steps with steps for simultaneously depositing an isotropic polymer/inhibitor to minimize lateral etching thereby allowing openings to be etched to a depth of 500 μm or more while retaining substantially uniform lateral dimensions (i.e. straight sidewalls). The deep etch step using the Bosch process can be terminated upon reaching the first silicon nitride layer 48.

Figure 4G:
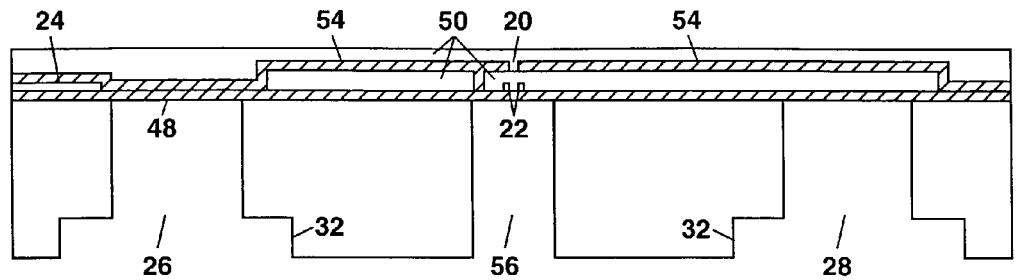
Figure 4H:
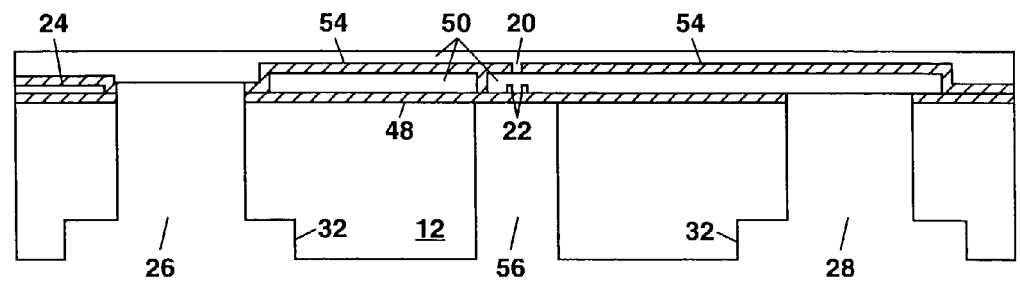

In FIG. 4G, an optional counterboring etch step can be carried out to enlarge the openings for the various ports 26, 28, 36 and 36' to facilitate the coupling of capillary tubing 30 to the apparatus 10. The counterboring etch step can be performed by enlarging the etch mask to a diameter of, for example, 300 μm and then using the Bosch etch process to etch partway through the substrate 12 to accept the capillary tubing 30. The optical access port 56 can also be counterbored, if needed, although this is not shown in FIG. 4G. With the various ports 26, 28, 36 and 36' formed, an anisotropic reactive ion etch step can then be used to etch through the first and second silicon nitride layers 48 and 52 as shown in FIG. 4H with the optical access port 56 being masked to prevent etching through the first silicon nitride layer 48 at this location.

Figure 4I:
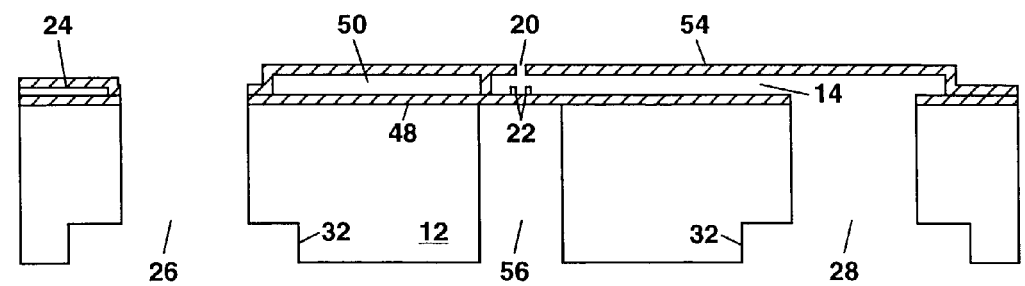

In FIG. 4I, the sacrificial material 50 can be removed as shown to open up the lower chamber 14 and the various ports 26, 28, 36 and 36' and passage ways thereto. This can be done by contacting exposed portions of the sacrificial material 50 to a selective wet etchant comprising hydrofluoric acid (HF) over a time period of generally several hours or overnight. Some unexposed portions of the sacrificial material 50, which have been completely encapsulated by the silicon nitride layers 48 and 54 as shown in FIG. 4I, can be left in place to strengthen sidewalls of the lower chamber 14 and passages to the inlet/outlet ports 36 and 36'. An outline shape 58 of the encapsulated sacrificial material 50 can be seen in FIG. 1.

Once the surface micromachining process is completed in FIG. 4I, the microcapillary tubing 30 can be attached to the various ports 26, 28, 36 and 36' as previously described with reference to FIGS. 2A and 2B, and the molded polymer material 40 can be attached to the substrate 12 to complete the upper chamber 16. The apparatus 10 can then be used with commercially-available patch-clamp electronics (e.g. voltage or current sources, signal amplifiers, and recording electronics) designed for ion channel analysis. Generally, this involves positioning the apparatus 10 under a microscope, making electrical connections between the patch-clamp electronics and the electrodes 22 and 24 (e.g. with electrical probes connected to the contact pads 44), adding the fluid and cells 100 through the sample entry/exit port 26 with a vacuum source connected to the fluid evacuation port 28, and introducing particular chemical species into the upper chamber 16 using the fluid entry/exit ports 36 and 36' as needed to analyze a response of one or more cells 100 thereto.

Figure 5:
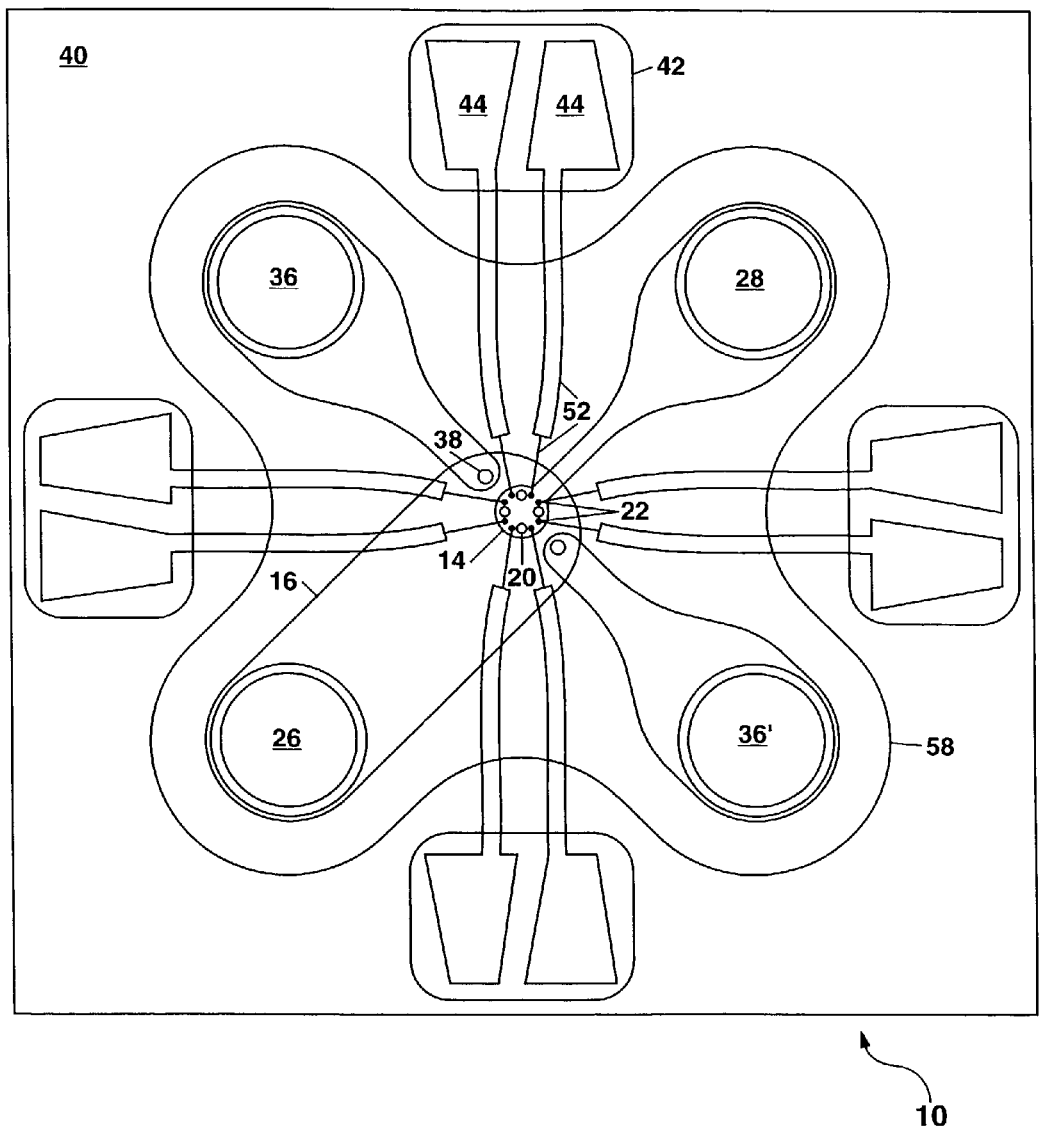
FIG. 5 schematically illustrates in plan view a second embodiment of the micromachined patch-clamp apparatus of the present invention.

FIG. 5 shows a schematic plan view of a second embodiment of the micromachined patch-clamp apparatus 10 of the present invention. This second embodiment of the apparatus 10 can be used for analyzing multiple cells 100 at the same time or sequentially. The second embodiment of the apparatus 10 in FIG. 5 is similar to the first embodiment of FIGS. 1 and 2A, 2B except that a plurality of openings 20 have been formed through the common wall 18, with each opening 20 being centered about a pair of electrodes 22 which can be located in the lower chamber 14, and with each pair of the electrodes 22 being connected to a different set of contact pads 44.

The apparatus 10 of FIG. 5 allows a plurality of cells 10 of the same or different types to be captured at the openings 20 so that the electrical characteristics of each cell 100 can be independently measured using the patch-clamp technique. The apparatus 10 of FIG. 5 allows multiple cells 100 to be processes simultaneously to ensure that a giga-ohm seal can be formed with at least one of the cells 100 and increases the speed at which measurements with the patch-clamp technique can be made as compared to the device 10 of FIG. 1. Additionally, the apparatus 10 of FIG. 5 can allow multiple sets of data to be obtained from cells 100 that are exposed to the same chemical stimulation. The second embodiment of the present invention in FIG. 5 can be formed similar to the first embodiment using the various process steps described with reference to FIGS. 3A and 3B and 4A-4I with minor modifications as required to form the multiple openings 20, electrodes 22, wiring 52 contact pads 44 and openings 42 in the molded polymer material 40.

Figure 6:
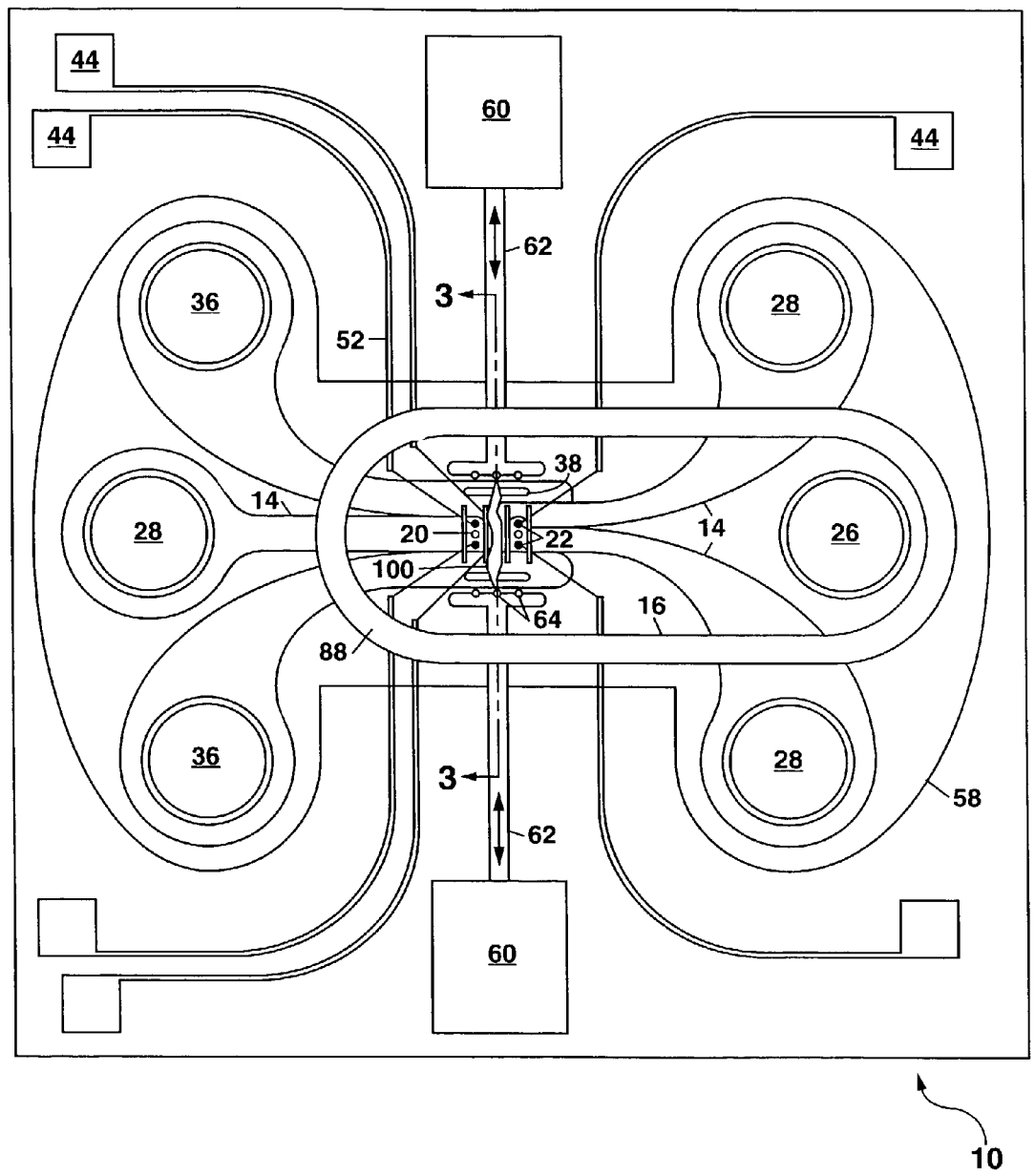
FIG. 6 schematically illustrates in plan view a third embodiment of the micromachined patch-clamp apparatus of the present invention that provides for mechanical stimulation of one or more cells during analysis using the patch-clamp technique.

FIG. 6 shows a schematic plan view of a third embodiment of the micromachined patch-clamp apparatus 10 of the present invention. In FIG. 6, the molded polymer material 40 has been omitted for clarity although this material 40 is shown in the cross section view of FIG. 7 along the section line 3-3 in FIG. 6.

Figure 7:
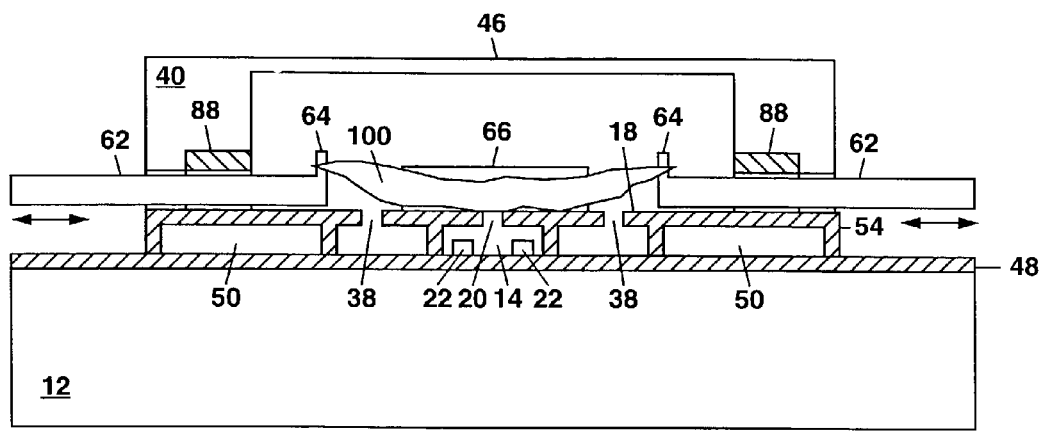
FIG. 7 shows a schematic cross-section view of the device of FIG. 6 along the section line 3-3 in FIG. 6.

The apparatus 10 in FIG. 6 includes a plurality of additional layers of deposited and patterned polysilicon that are used to form one or more electrostatic actuators 60 on the substrate 12. The electrostatic actuators 60 can be operatively connected to a biological cell 100 (e.g. an elongate muscle cell) to provide mechanical stimulation to the cell 100 during analysis with the patch-clamp technique. Each electrostatic actuator 60 can be mechanically coupled through a linkage 62 formed from the additional polysilicon layers, with the linkage 62 being terminated by one or more attachment points 64 (e.g. in the form of upward-extending posts) that can be used to form an attachment to a biological cell 100 which is captured above an opening 20 as described previously. A plurality of elongate ribs 66 can be provided as shown in FIGS. 6 and 7 to extend slightly upward above the common wall 18 to facilitate aligning the cell 100 (e.g. the elongate muscle cell) between a pair of the attachment points 64. In certain embodiments of the present invention, these ribs 66, which are electrically conducting, can be connected to additional contact pads 44 so that a voltage can be placed across the cell 100 for electrical stimulation of the cell 100, or for electroporation.

To attach the biological cell 100 to the attachment points 64 on either side of the cell 100, a protein can be provided through the fluid entry/exit ports 36 and corresponding orifices 38 to coat the attachment points 64 and each side of the cell 100. The protein can then interact with the cell membrane to adhere the cell 100 to the attachment points 64.

With the cell 100 adhered to the attachment points 64, an actuation voltage (e.g. 10-100 Volts) can be applied to one or both of the electrostatic actuators 60 to move the linkage 62 forward or backward in the direction shown by the double-ended arrows in FIGS. 6 and 7 to push or pull on the cell 100. The apparatus 10 in FIGS. 6 and 7 is useful for measuring the effect of such mechanical stimulation on particular cells 100 including muscle cells and nerve cells using the patch-clamp technique. In the device 10 of FIGS. 6 and 7, provision has been made for capturing and studying up to three cells 100 at a time, with three different evacuation ports 28 being provided in the apparatus 10, and with each evacuation port 28 being connected to a single opening 20. Additionally, with the actuation voltage removed from the electrostatic actuator 60, the cell 100 can be electrically or chemically stimulated to contract or relax, and a capacitance of the electrostatic actuator 60 can be sensed to measure the movement of the cell 100 and a force produced thereby. Although not shown in FIG. 7, an optical access port 56 can be optionally formed through the substrate 12 during etching of the various ports 26, 28 and 36 as has been described previously.

Electrostatic actuators 60 that can be used with the present invention include parallel-plate electrostatic actuators and electrostatic comb actuators. Such electrostatic actuators 60 can provide movement that is generally in the range of 2-20 μm. A particular type of electrostatic actuator 60 that can be used in the apparatus 10 of FIGS. 6 and 7 is a compact electrostatic comb actuator 60 as illustrated in FIG. 8 which provides about 2 µm of movement and which can be used in combination with a pivotless compliant structure 68 which provides up to a ten times or more increase in displacement in return for a corresponding decrease in actuation force.

The compact electrostatic comb actuator 60 has been described in detail in U.S. Pat. No. 6,133,670 which is incorporated herein by reference. Briefly, the compact electrostatic comb actuator 60 comprises one or more stationary electrostatic combs 70 formed on the substrate 12 from a plurality of stacked polysilicon layers, with each stationary electrostatic comb 70 having a mating moveable electrostatic comb 72 formed from at least a portion of the same polysilicon layers. The moveable electrostatic combs 72 are suspended above the substrate 12 by underlying springs (not shown) formed from one or more of the polysilicon layers and are attached to a rigid polysilicon frame 74 which can include a truss 76 for concentrating an electrostatic force produced by the actuator 60. Fabrication of the compact electrostatic comb actuator 60 is performed by surface micromachining wherein the plurality of polysilicon layers are deposited and patterned to build up the structure of the actuator 60 layer by layer, and with adjacent polysilicon layers being separated by a layer of the sacrificial material 50 as needed to provide air-gap spacings between particular elements therein (e.g. between the moveable electrostatic combs 72 and the first silicon nitride layer 48 on the substrate 12).

The pivotless compliant structure 68 (also termed a displacement multiplying structure) has been described in detail in U.S. Pat. No. 6,175,170 which is incorporated herein by reference. This structure 68 comprises a plurality of interconnected flexible beams 78 formed from polysilicon or silicon nitride or both, with the beams 78 being arranged to provide a displacement at an output end 80 of the structure 68 which is larger than the displacement at an input end 82 thereof. Some of the beams 78 are attached to the substrate 12 through anchors 84, while the remaining beams 78 are suspended above the substrate 12. The beams 78 can be formed from a plurality of layers of polysilicon or silicon nitride or both which are stacked and interconnected together to provide a high out-of-plane rigidity while providing flexibility for motion in the plane of the substrate 12. Each beam 78 can be, for example, up to 10 µm high and 1-2 µm wide. In the pivotless compliant structure 68 of FIG. 8, motion of the electrostatic comb actuator 60 along an axis 86 and in a direction indicated by the short arrow results in motion at the output end 80 of the structure 68 which is along the same axis 86 in the opposite direction as indicated by the long arrow.

Figure 8:
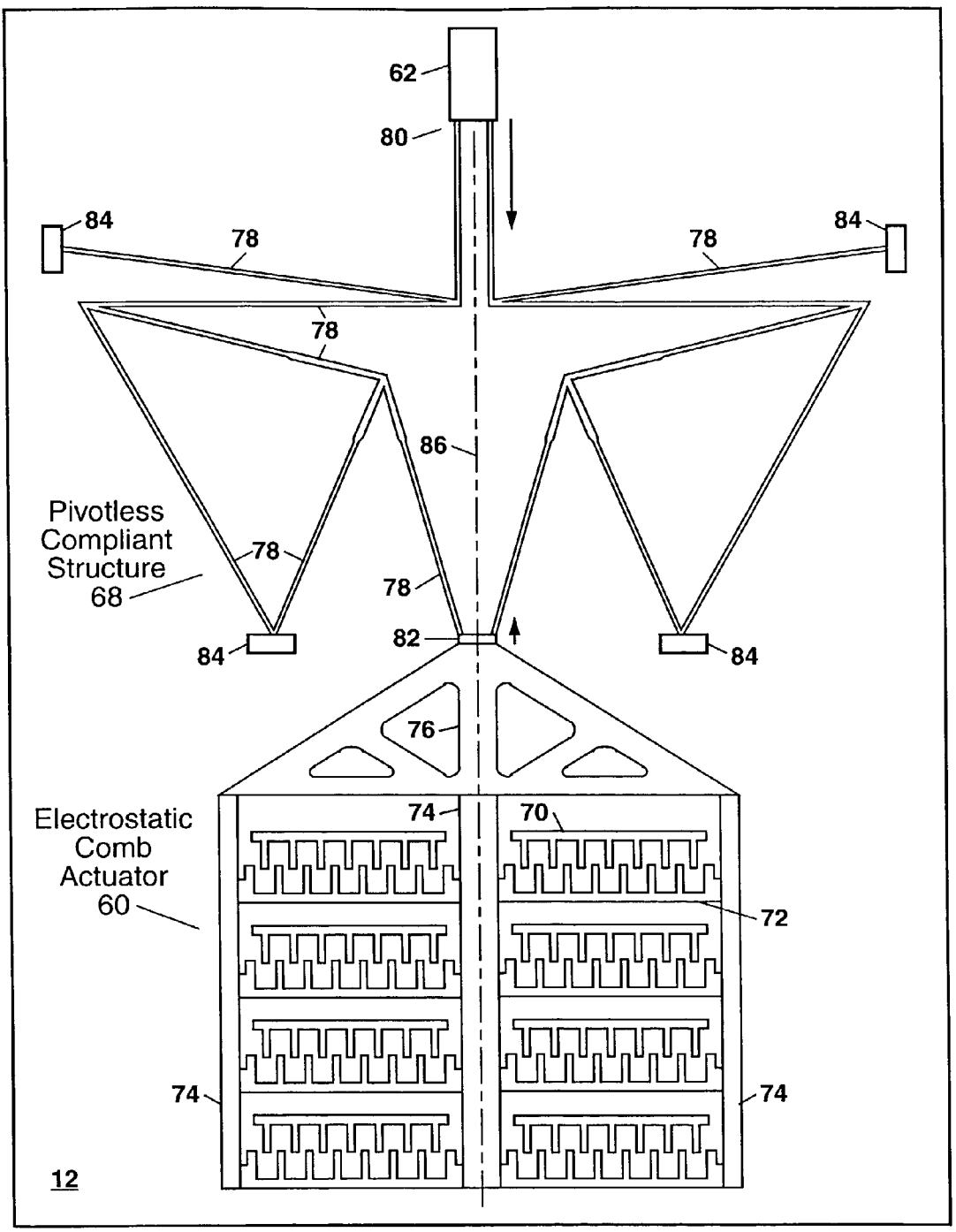
FIG. 8 schematically illustrates in plan view a compact electrostatic comb actuator and a pivotless compliant structure that can be used to provide the mechanical stimulation for the device of FIG. 6.

The application of an actuation voltage to the compact electrostatic comb actuator 60 in FIG. 8 thus acts to pull on the cell 100 located in the apparatus 10 of FIGS. 6 and 7 through the attachment of the cell 100 to the end of the linkage 62; whereas removing the actuation voltage results in motion of the linkage 62 in the opposite direction and can push against the cell 100. Other configurations of the pivotless compliant structure 68 allow motion in the opposite direction in response to motion of the compact electrostatic comb actuator 60. Thus, for example, in FIG. 6 one electrostatic comb actuator 60 can be configured to pull on the cell 100 and another actuator 60 can be configured to push against the cell 100. This would allow the effect of both types of motion (i.e. pushing and pulling) on the cell 100 to be analyzed using the patch-clamp technique.

The compact electrostatic comb actuator 60 and the pivotless compliant structure 68 in FIG. 8 can be fabricated using conventional surface micromachining from a plurality of deposited and patterned layers of polysilicon and the sacrificial material 50 which are provided above the second silicon nitride layer 54. Electrical connections to the compact electrostatic comb actuator 60 are preferably formed from the same layer of polysilicon used to form the electrodes 22 and the wiring 52. This can be done by forming openings through the silicon nitride layers 48 and 54 and any intervening sacrificial material 50 and interconnecting subsequently deposited polysilicon layers to the layers used to form the electrodes 22 and wiring 52.

The deposited and patterned layers of polysilicon are also used to form the linkage 62 and a wall 88 defining a part of the upper chamber 16 through which the linkage 62 penetrates. A small gap (e.g. 1 µm) between each side of the linkage 62 and an opening through the wall 88 allows the linkage 62, which is suspended above the substrate 12, to move forwards and backwards through the wall 88 to mechanically stimulate the cell 100 while preventing any substantial leakage of the fluid from the upper chamber 16. Surface tension of the fluid within the gap between the linkage 62 and the wall 88 also helps to prevent leakage of the fluid.

Other embodiments of the present invention can be formed with other types of electrostatic actuators 60 as known to the art. For example, an electrostatic actuator 60 comprising a plurality of capacitively-coupled electrostatic plates as disclosed in U.S. Pat. No. 6,507,138, which is incorporated herein by reference, can be substituted for the compact electrostatic comb actuator 60 in FIG. 8 and used in combination with the pivotless compliant structure 68. In some embodiments of the present invention, the pivotless compliant structure 68 can be omitted (e.g. when the displacement provided by the electrostatic actuator 60 is sufficient so that no displacement multiplication is needed).

The matter set forth in the foregoing description and accompanying drawings is offered by way of illustration only and not as a limitation. Other applications and variations of the present invention will become evident to those skilled in the art. The actual scope of the invention is intended to be defined in the following claims when viewed in their proper perspective based on the prior art.

What is claimed is:

1. A micromachined patch-clamp apparatus for analyzing a biological cell, comprising:
    (a) a silicon substrate;
    (b) a pair of fluid chambers formed above the silicon substrate, with the pair of fluid chambers having a common wall oriented parallel to the plane of the substrate, with the common wall comprising silicon nitride and having an opening therethrough between the pair of fluid chambers, and with a lower chamber of the pair of fluid chambers having at least one electrode therein, and with an upper chamber of the pair of fluid chambers comprising a molded polymer material which forms a removable closed top over the upper chamber, with the upper chamber being adapted to receive the biological cell for analysis thereof; and
    an electrostatic actuator operatively connected through another opening in a sidewall of the upper chamber to provide mechanical stimulation to the biological cell located in the upper chamber.

* * * * *